United States Patent [19]

Strojny et al.

[11] 4,113,745
[45] Sep. 12, 1978

[54] CATALYST FOR AND METHOD OF PRODUCING MALEIC ANHYDRIDE

[75] Inventors: Edwin J. Strojny, Midland, Mich.; Hans R. Friedli; Milton S. Wing, both of Lake Jackson, Tex.

[73] Assignee: The Dow Chemical Company, Midland, Mich.

[21] Appl. No.: 828,409

[22] Filed: Aug. 29, 1977

[51] Int. Cl.$^2$ .......................................... C07D 307/60
[52] U.S. Cl. .............................. 260/346.75; 252/464; 252/455 R
[58] Field of Search ................................ 260/346.75

[56] References Cited

U.S. PATENT DOCUMENTS 2,079,490  5/1937  Conover .......................... 260/533 N

FOREIGN PATENT DOCUMENTS 21,093  1973  Japan.

*Primary Examiner*—Henry R. Jiles
*Assistant Examiner*—Bernard Dentz
*Attorney, Agent, or Firm*—G. R. Baker

[57] ABSTRACT

A catalyst for, and method of, producing a reaction product predominantly of maleic anhydride, that is a product of reaction containing a ratio of maleic to citraconic anhydrides of at least 25 to 1, respectively, and preferably greater than about 100 to 1, respectively, by reacting a feed stream consisting of oxygen or an oxygen-containing gas and an organic $C_5$ feed predominantly of piperylene and dicyclopentadiene, and preferably predominantly dicyclopentadiene, at bath temperatures of from about 360° to about 450° C over a catalyst comprising a mixture of 25 to 60 weight percent titanium oxide ($TiO_2$), 5 to 40 weight percent molybdenum oxide ($MoO_3$) and 30 to 60 weight percent vanadium oxide ($V_2O_5$) on an alpha alumina or alumina-silica carrier having less than about one square meter per gram ($<1$ m$^2$/g) surface area. The feed rate of the reactants is preferably between about 1,500 and about 15,000 gas hourly space velocity; the $C_5$ hydrocarbon content of the feed gases being between about 0.5 and 1.8 volume percent.

3 Claims, 3 Drawing Figures

\* = DCPD DICYCLOPENTADIENE

CATALYST FOR AND METHOD OF PRODUCING MALEIC ANHYDRIDE

BACKGROUND OF THE INVENTION

The oxidation of various organic compounds to prepare maleic and citraconic acid, while well documented in the literature, is abstracted here.

Conover in U.S. Pat. No. 2,079,490 (1937) disclosed the oxidation of cyclopentadiene and polymeric cyclopentadiene to maleic anhydride over any good catalyst for oxidation of organic materials to form carboxylic acids. The metals of the fifth and sixth group of the Periodic Table were disclosed and vanadium oxide on a support was illustrated.

Milas et al. in U.S. Pat. No. 2,136,144 disclose the oxidation of naphthenes over similar catalysts, viz., elements of the fifth and sixth groups of the Periodic System, specifically, vanadium, bismuth, molybdenum, tungsten, etc., supported on an inert carrier. Yields of maleic acid of 10 to 20.5 percent were reported.

Faith and Dendurent, *Refiner & Natural Gasoline Manufacturer*, Vol. 18, No. 10, Oct. 1939, pp. 61–64, disclosed the conversion of amylene to maleic anhydride over a vanadium pentoxide catalyst. $C_{6-8}$ olefinic hydrocarbons were reported to give even better yields than amylene.

Numerous patents have issued since 1939 disclosing specific catalyst composition reporting the results in preparing maleic and citraconic acids and anhydrides, to wit: U.S. Pat. Nos. 2,649,477; 2,719,853; 3,086,026; 3,106,569; 3,156,705; 3,156,706; 3,156,707; 3,366,648; and 3,464,930 to list but a few. U.S. Pat. No. 3,086,026 disclosed a $V_2O_5/MoO_3$, ratio of 1 to 1 to 1 to 8, respectively, with 0.2 to 1.25 percent $P_2O_5$ and 60–80 percent $TiO_2$ on a support. U.S. Pat. No. 3,106,569 disclosed a 50–90 atomic percent vanadium, 5–45 at. percent Mo and 2–30 at. percent Ti on an inert support. Skinner & Tieszen (1961) reported an improved catalyst of 3V/9Mo/1P on $SiO_2$ gel and Mitsubishi Chemical Industries has disclosed a V-Mo-P on $SiO_2$ and a V-P on $SiO_2$ as suitable catalysts.

BRIEF DESCRIPTION OF THE INVENTION

An especially prepared $C_5$ hydrocarbon stream containing predominantly a mixture of cis- and trans-piperylene and dicyclopentadiene and co-dimers; that is a $C_5$ stream which has been distilled to remove the components boiling below isoprene and all or a major portion of the isoprene, and more preferably a feed stream composed of over 90 percent dicyclopentadiene and co-dimers, the remainder being benzene and heavies, is oxidized with oxygen or an oxygen-containing gas over a catalyst which is a 3 to 20 weight percent of a mixture of 30 to 60 weight percent vanadium oxide, 5 to 40 weight percent molybdenum oxide and 25 to 60 weight percent titanium oxide on an alpha alumina or alumina-silica support having a surface area of less than 1 square meter per gram ($<1$ m$^2$/g).

The catalyst is prepared by impregnating the support with a mixture of aqueous solutions of the salts of the active ingredients, drying and calcining the so-prepared catalyst at about 500° C for at least 2 hours.

The especially prepared feeds for use in accordance with the present invention are those in which isoprene and its precursors, monoolefins and saturates, and lights have been substantially, removed and cyclopentadiene has been converted into dicyclopentadiene and its codimers. Three techniques to achieve this are illustratively described in FIGS. 1, 2 and 3 of the drawings. In FIG. 1 a crude $C_5$ stream is subjected to heat-soaking for about 8 to 32 hours at about 80° to 100° C during which time dimerization occurs, thereafter the heat-soaked product if not used as feed, is distilled to remove isoprene and light hydrocarbons boiling below isoprene. The bottoms from this distillation is suitable as a feed for the present process and contains predominantly dicyclopentadiene, its co-dimers and piperylene. This product may be further distilled to separate the dicyclopentadiene and its co-dimers from the piperylene and the dicyclopentadiene used as a preferred feed in accordance with the present invention. FIG. 2 shows an alternative procedure to obtaining a de-lighted heat-soaked product which can be used as a feed or which can be further distilled to obtain a dicyclopentadiene/co-dimer fraction which can be used as a feed and an overhead which can further be separated into its predominant fractions. Finally, as shown in FIG. 3, is a further alternative procedure for obtaining a heat-soaked and de-lighted heat-soaked feed as well as a dicyclopentadiene/co-dimer concentrate for use as a feed. An alternative method, not shown is to heat soak the crude $C_5$ stream as in all other schemes shown and hereabove described, then distill the heat soaked material to remove substantially all of the components boiling below dicyclopentadiene and co-dimers, that is, remove the mono- and diolefins including isoprene and the piperylenes to obtain as a bottom cut the dicyclopentadienes and co-dimers. This bottom cut may be used as a starting material for the present invention or it may be combined with the piperylene cut subsequently obtained during the recovery of isoprene from the distillations of the overhead from this distillation. In practice the overhead is subjected to extractive distillation to separate the monoolefins and saturates from the diolefins (mainly isoprene and piperylenes) which latter, the diolefins, are further distilled to recover the isoprene. The bottoms cut from this distillation, predominantly the piperylenes, are useful per se in accordance with the present process or may be combined with the bottom cut of the first distillation of this alternative process and the mixture used as a starting material for the present invention. The various compositions obtained by treatment in accordance with the procedure of FIG. 3 are representatively set forth in the following table.

TABLE I

| | FEEDSTOCK COMPOSITIONS | | | |
| --- | --- | --- | --- | --- |
| | Crude C5 | Crude C5[1] | | |
| Components | Heat-Soaked (C5-HS) | Heat-Soaked De-lighted (C5-HSDL) | Pipery-lene[2] + DCPD | DCPD Concentrate[3] |
| Isopentane | 10.0 | .2 | | |
| 3-Methyl-Butene-1 | .7 | .1 | | |
| n-Pentane | 16.2 | .2 | | |

TABLE I-continued

| | FEEDSTOCK COMPOSITIONS | | | |
|---|---|---|---|---|
| | Crude C5 | Crude C5[1] | | |
| Components | Heat-Soaked (C5-HS) | Heat-Soaked De-lighted (C5-HSDL) | Pipery-lene[2] + DCPD | DCPD Concentrate[3] |
| Pentene-1 | 2.7 | 5.2 | 1.5 | |
| 2-Methyl-Butene-1 | 4.3 | .7 | | |
| cis-trans-Pentene-2 | 2.5 | 7.2 | 2.2 | |
| 2-Methyl-Butene-2 | 2.1 | 2.2 | 1.4 | |
| Isoprene | 17.4 | 15.6 | 3.4 | |
| Cyclopentene | 3.7 | 10.9 | 14.5 | |
| cis-, trans-Piperylene | 9.9 | 25.4 | 24.5 | |
| Cyclopentadiene | 2.6 | 3.4 | 1.4 | |
| Benzene | .9 | 1.8 | | 1.0 |
| DCPD and codimers | 17.0 | 21.0 | 48.0 | 95.5 |
| Heavies | | 2.5 | 2.0 | 3.5 |

[1]Derived by distillation of crude $C_5$ fraction after heat-soaking (C5-HSDL).
[2]Derived by distillation of C5-HSDL cut.
[3]Derived by distillation of piperylene + DCPD cut.

DETAILED DESCRIPTION OF THE INVENTION

Catalyst Preparation

Figure 1:
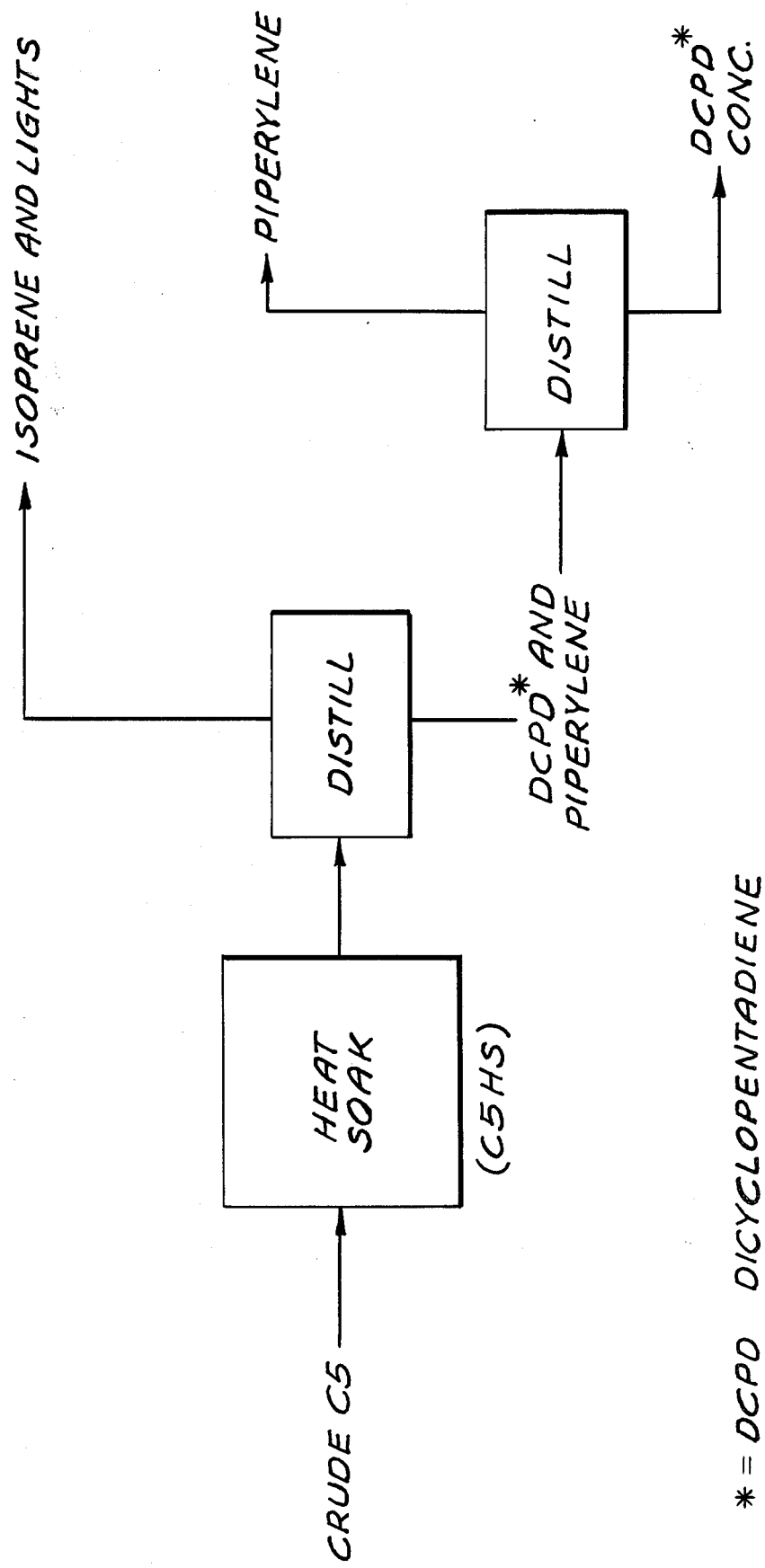
Figure 2:
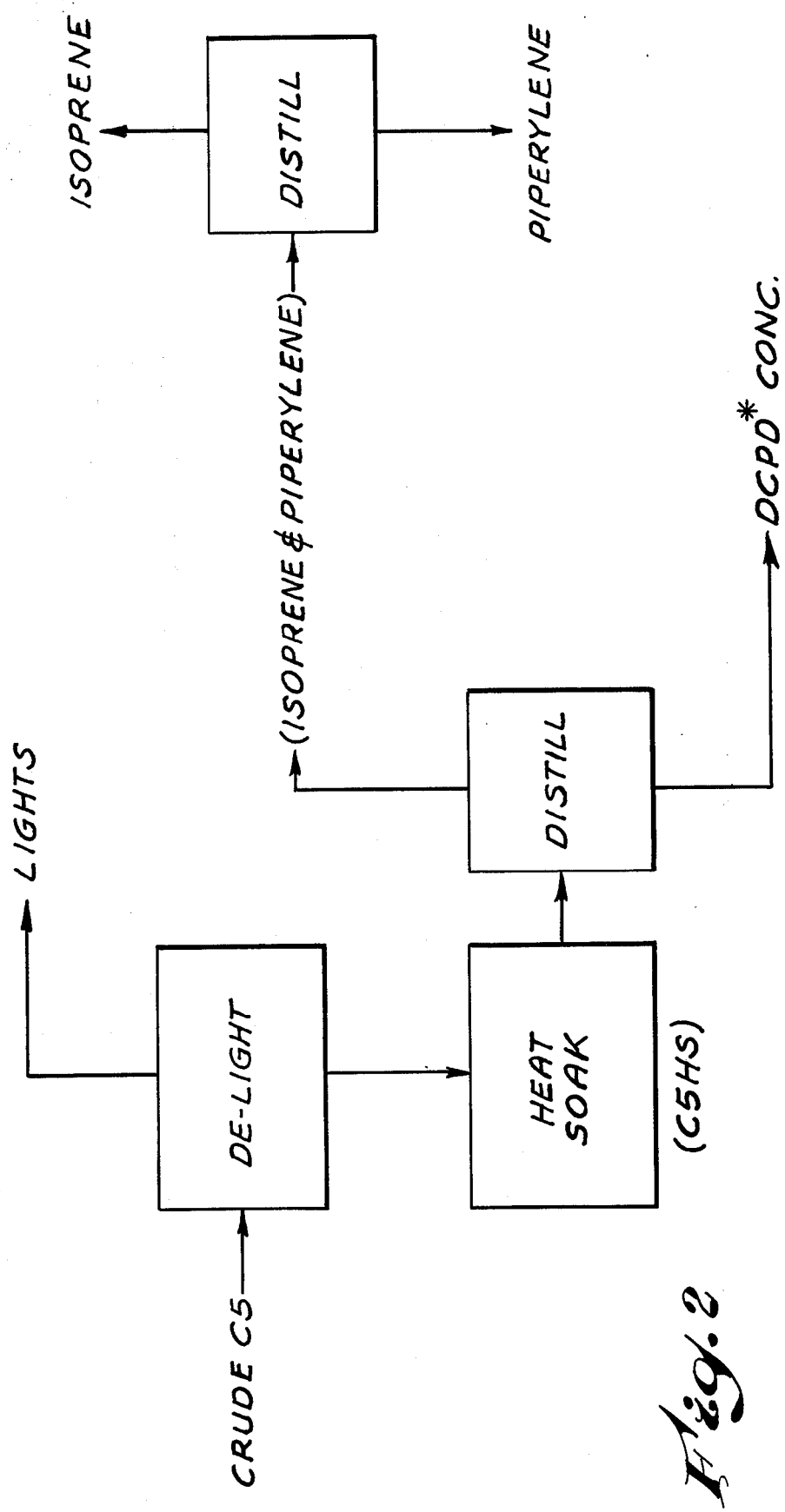
Figure 3:
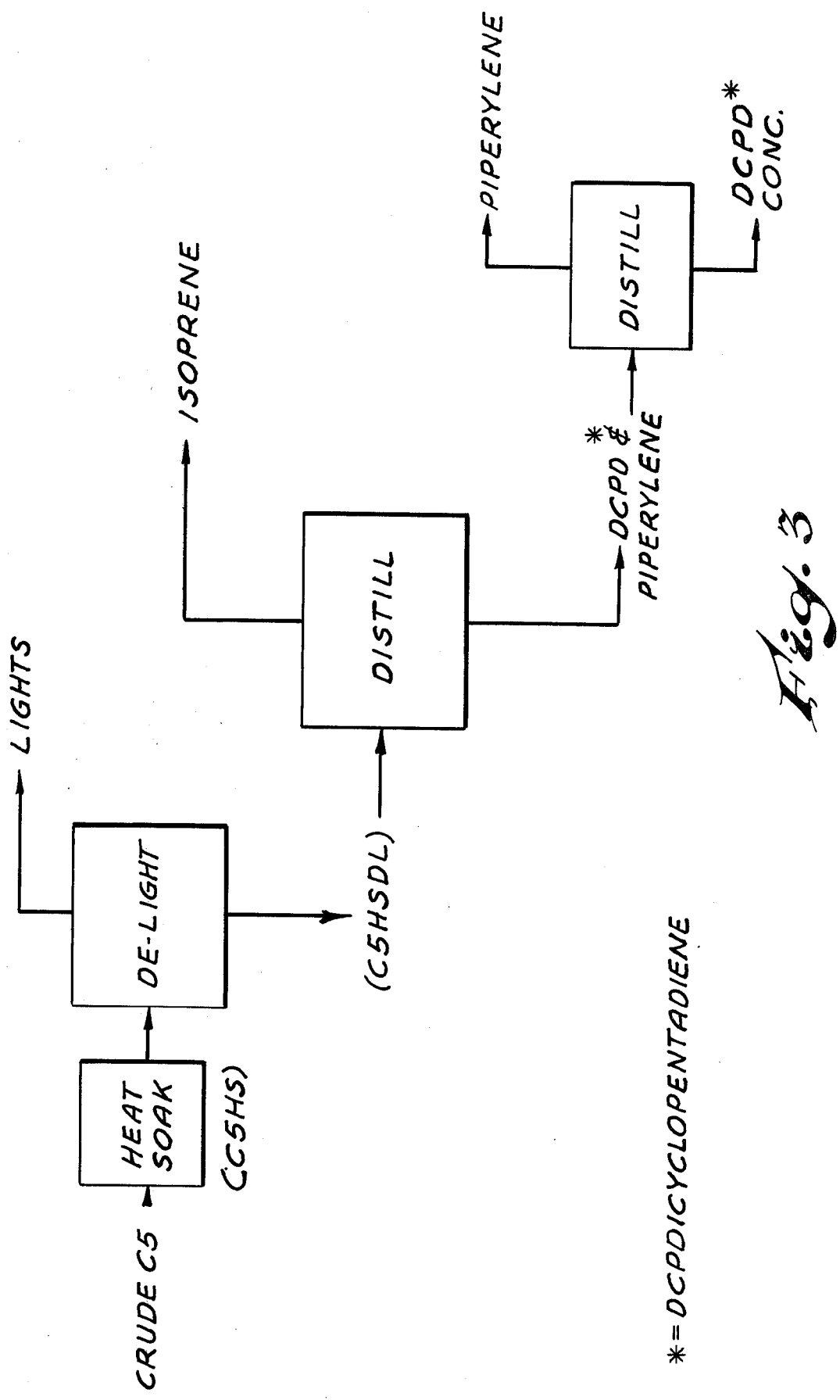

General Procedure:

Vanadium pentoxide ($V_2O_5$) was reduced with oxalic acid dihydrate in water on a steam bath and ammonium molybdate (($NH_4)_6Mo_7O_{24}\cdot 4H_2O$) was dissolved in water. The two solutions were combined and heated (70°–90° C) overnight. Titanium oxide ($TiO_2$) was added, the mixture stripped for 2 hours on a steam bath and then sprayed onto alumina-silica spheres, Norton SA 5205, 3/16 to ⅜ inch, while tumbling the spheres. The spheres were then dried at room temperature in an air stream, then at 130° C. Thereafter, the spheres were heated to 400° C at a rate of 100° C per hour. Finally, the spheres were calcined at 500° C for 2 hours, cooled, sieved to remove the fines, the catalyst loading determined and then tested in the laboratory according to the following General Oxidation Procedure.

Process Parameters

General Oxidation Procedure:

A U-tube, ⅜ inch O.D., ca ½ inch I.D. stainless steel, was immersed in a salt bath. About 12 cm³ of a catalyst, prepared as above, crushed and screened to −5 to +12 screen, was introduced into the upflow side of the tube. A ⅛ inch thermowell was positioned in the catalyst bed. The reaction mixture entered the downflow side of the tube. Liquid feed was metered with capillary tubing; gas feed with a gas flow meter. Products were condensed at 5°–15° C and water-scrubbed. The combined products were analyzed by liquid chromatography for maleic anhydride and citraconic anhydride. The hydrocarbon conversion was essentially complete.

The following table illustrates the results employing the catalysts of the present invention. The yield is expressed in weight percent based on total feed fed into the reactor. Liquid flows were in the range of up to 6 gm/hr, care being taken to maintain concentrations outside the explosive limits in air. Air flows were from 72 to 144 liters per hour. Experimental results are reported in Table II as follows:

First line—
  % loading (catalyst composition) on Norton SA 5205 alumina-silica spheres crushed to −5 to +12 screen.

Second line—
  Feedstock origin, % by volume hydrocarbon in air, gas hourly space velocity $hr^{-1}$, bath temperature in ° C and yields as percent of maleic anhydride and citraconic anhydride, based on weight percent hydrocarbon fed.

The above procedure was employed to react the below-enumerated feeds with air over the catalyst. The results are tabulated below.

TABLE II

SUMMARY OF OXIDATION RUNS

| Example | Feed (Origin) | (% Vol) | GHSV ($hr^{-1}$) | Bath Temperature ° C | Yields % MA | % CA |
|---|---|---|---|---|---|---|
| 1 | 14.6% (70% [2V/1Mo] + 30% $TiO_2$) SA 5205 | | | | | |
| | $C_5$-HSDL | 1.01 | 6000 | 406 | 50.6 | 7.3 |
| | DCPD Conc. | .66 | 8000 | 412 | 78.0 | 0.5 |
| | Pip/DCPD | .75 | 8000 | 417 | 64.9 | 1.9 |
| 2 | 11.4% (60% [4.67V/1 Mo] + 40% $TiO_2$)SA 5205 | | | | | |
| | $C_5$-HSDL | .95 | 8000 | 398 | 51.1 | 7.7 |
| | DCPD Conc. | .70 | 8000 | 428 | 80.4 | 0.5 |
| | Pip/DCPD | .73 | 8000 | 425 | 67.3 | 2.6 |
| 3 | 13.9(50%[4.67 V/1 Mo] + 50% $TiO_2$)SA 5205 | | | | | |
| | $C_5$-HSDL | .97 | 8000 | 384 | 51.7 | 8.2 |
| | DCPD Conc. | .65 | 8000 | 408 | 81.1 | 0.0 |
| | Pip/DCPD | .81 | 8000 | 410 | 64.8 | 2.0 |
| 4 | 10.3%(70%[9V/1 Mo]/0.45 P + 30% $TiO_2$)SA 5205 | | | | | |
| | $C_5$-HSDL | .84 | 12000 | 422 | 49.3 | 7.4 |
| | Pip/DCPD | .82 | 12000 | 421 | 60.0 | 7.8 |
| | DCPD Conc. | .86 | 12000 | 436 | 68.4 | 0.2 |
| | Crude $C_5$ | 1.22 | 12000 | 422 | 24.5 | 10.0 |
| 5 | 10.86%[4.67V/1 Mo]SA 5205 | | | | | |
| | $C_5$-HSDL | .89 | 6000 | 443 | 50.8 | 6.0 |

TABLE II-continued
SUMMARY OF OXIDATION RUNS

| Example | Feed (Origin) | (% Vol) | GHSV (hr$^{-1}$) | Bath Temperature °C | Yields % MA | % CA |
|---|---|---|---|---|---|---|
| 6 | 12.6%[50%(4.67V/1 Mo) + 50% TiO$_2$]SA 5205 | | | | | |
| | DCPD Conc. | 1.02 | 6000 | 430 | 75.7 | 0.0 |
| | Pip/DCPD | 0.85 | 8000 | 417 | 62.5 | 2.3 |
| 7 | 7.9%[80%(4.67V/1 Mo) + 20% TiO$_2$]SA 5205 | | | | | |
| | DCPD Conc. | 1.0 | 6000 | 435 | 75.6 | 0.0 |
| | Pip/DCPD | 0.8 | 8000 | 433 | 61.4 | 1.5 |
| 8 | 18.6%[30%(4.67V/1 Mo) + 70% TiO$_2$]SA 5205 | | | | | |
| | DCPD Conc. | 1.03 | 6000 | 422 | 70.3 | 0.0 |
| | Pip/DCPD | .79 | 8000 | 416 | 64.1 | 2.4 |
| 9 | 6.68%(4.67V/1 Mo)SA 5205 | | | | | |
| | DCPD Conc. | 1.03 | 6000 | 438 | 65.9 | 0.3 |
| | Pip/DCPD | .82 | 8000 | 454 | 57.1 | 1.7 |
| 10 | 10.9%[9V/1 Mo]SA 5205 | | | | | |
| | C$_5$-HSDL | .89 | 12000 | 428 | 48.9 | 6.9 |
| | DCPD | 1.03 | 10000 | 399 | 75.9 | 0.0 |
| | Piperylene | .99 | 12000 | 408 | 51.0 | 5.1 |

Additional experiments were run employing catalysts of four references. The results are set forth below:

TABLE III
SUMMARY OF OXIDATION RUNS

| Example | Feed (Origin) | (% Vol) | GHSV (hr$^{-1}$) | Bath Temperature °C | Yields % MA | % CA |
|---|---|---|---|---|---|---|
| 1 | Halcon benzene oxidation catalyst, British 1371653 (74) 10.29% (1.0 V$_2$O$_5$/.87 MoO$_3$ 0.083 B$_2$O$_3$/0.096 Na$_2$O/0.028 P$_2$O$_5$/0.042 CoO$_3$)SA 5205 | | | | | |
| | C$_5$-HSDL | 1.0 | 8000 | 437 | 43.7 | 4.8 |
| 2 | JAP. DCPD/CPD Catalyst, Jap. Pat. Publ. 21,093/1973 8.35% (1.0 V$_2$O$_5$/0.2 MoO$_3$/0.01 Na$_2$O/0.01 P$_2$O$_5$/0.03 NiO)SA 5205 | | | | | |
| | C$_5$-HSDL | .95 | 6000 | 447 | 51.1 | 4.8 |
| | 95% DCPD | .74 | 6000 | 438 | 76.9 | 0.0 |
| | DCPD Conc. | .74 | 6000 | 447 | 71.7 | 0.0 |
| | Pip/DCPD | .71 | 6000 | 446 | 54.1 | 2.2 |
| 3 | Monsanto Example 3 U.S. 3,106,569(63), Benzene 7.25% [92.4% (8.1V/1 Mo) + 7.6% TiO$_2$]SA 5205 | | | | | |
| | DCPD Conc. | 1.02 | 6000 | 428 | 72.9 | 0.0 |
| | Pip/DCPD | .79 | 8000 | 430 | 59.1 | 1.0 |
| 4 | BASF, Example 3 U.S. 3,086,026(63), Benzene 100% [35.8% (1.2V/1 Mo/0.08P) + 64.2% TiO$_2$]unsupported | | | | | |
| | DCPD Conc. | .95 | 6000 | 431 | 58.7 | 0.0 |
| | Pip/DCPD | .81 | 8000 | 400 | 59.7 | 0.8 |

Data obtained employing the present invention compared to the most closely related prior art known at the time the invention was made illustrates the superior results obtainable employing the present invention, and establishes the necessity for the presence of titanium oxide as a component of the catalyst even when employing the most advantageous feedstock.

Effect of TiO$_2$ on Yields to MA from C$_5$ (HSDL), Piperylene/DCPD and DCPD Concentrate

| TiO$_2$ Concentration | Example | C$_5$(HSDL) MA | C$_5$(HSDL) CA | Pip/DCPD MA | Pip/DCPD CA | DCPD Concentrate MA | DCPD Concentrate CA |
|---|---|---|---|---|---|---|---|
| 0% (1) 6.68% (4.67/1, V/Mo) | 12 | — | — | 57.1 | 1.7 | 65.9 | 0.3 |
| Japan. Pat. Publ. 21,093(73) | 2 | 51.1 | 4.8 | 54.1 | 2.2 | 71.7 | 0.0 |
| Halcon British 1,371,653 | 1 | 43.7 | 4.8 | — | — | — | — |
| (7.25% Monsanto) (Example 3, U.S. 3,106,569) | 13 | — | — | 59.1 | 1.0 | 72.9 | 0.0 |
| 20% (1) 7.9% (4.67/1, V/Mo) | 10 | — | — | 61.4 | 1.5 | 75.6 | 0.0 |
| 30% (1) 14.6% (4.67/1, V/Mo) | 3 | 50.6 | 7.3 | 64.9 | 1.9 | 78.0 | 0.5 |
| 40% (1) 11.4% (4.67/1, V/Mo) | 4 | 51.1 | 7.7 | 67.3 | 2.6 | 80.4 | 0.5 |
| 50% (1) 13.9% (4.67/1, V/Mo) | 5 | 51.7 | 8.2 | 64.8 | 2.0 | 81.1 | 0.0 |
| (64.2% BASF) (Example 3, U.S. 3,086,026) | 14 | — | — | 59.7 | 0.8 | 58.7 | 0.0 |
| 70% (1) 18.6% (4.67/1, V/Mo) | 11 | — | — | 64.1 | 2.4 | 70.3 | 0.0 |

(1) Catalyst prepared by Applicants with indicated % of a mixture of 4.67 to 1 vanadium to molybdenum on a support with indicated TiO$_2$ percentage.

These data illustrate that high (>60+) and low (<30−) TiO$_2$ contents give poorer yields to MA. This is particularly evident with DCPD Concentrate as feed, but can also be observed with Piperylene/DCPD.

The effect of the presence of titanium oxide is further illustrated in the fact that the presence of >20 and <60 weight percent of titanium oxide based on the total V$_2$O$_5$, MoO$_3$ and TiO$_2$ in the catalyst permits the use of slightly lower temperatures than catalysts without titanium oxide or greater than 60 percent titanium oxide without appreciable loss of conversion or yield of maleic anhydride to citraconic acid.

Effect of TiO$_2$ on Reaction Temperature

| % TiO$_2$ | DCPD Conc. Bath Temp.° C | Ratio MA/CA | Pip/DCPD Bath Temp.° C | Ratio MA/CA |
|---|---|---|---|---|
| 0 | 438 | 65.9/.3 | 454 | 57.1/1.7 |
| 20 | 435 | 75.6/0 | 433 | 61.4/1.5 |
| 50 | 430 | 75.7/0 | 417 | 62.5/2.3 |
| 70 | 422 | 70.3/0 | 416 | 64.1/2.4 |

-continued

| Effect of TiO$_2$ on Reaction Temperature | | | | |
|---|---|---|---|---|
| % TiO$_2$ | DCPD Conc. Bath Temp. °C | Ratio MA/CA | Pip/DCPD Bath Temp. °C | Ratio MA/CA |
| 7.25 | 428 | 72.9/0 | 430 | 57.1/1.7 |

We claim:

1. A process for preparing maleic anhydride which comprises treating a crude C$_5$ stream at a temperature of 80° to 100° C for about 8–32 hours, separating the resulting stream by distillation into an overhead stream of isoprene and components boiling below isoprene, and a bottoms stream comprised predominantly of piperylene and closely boiling C$_5$ hydrocarbons and dicyclopentadiene and its codimers, introducing the said bottoms stream and oxygen or an oxygen-containing gas, into a reaction zone containing a catalyst which comprises a mixture of vanadium oxide, molybdenum oxide, and titanium oxide supported on an inert carrier in an amount to supply from 3–20 weight percent of the mixture having a ratio of V$_2$O$_5$/MoO$_3$/TiO$_2$ of 25 to 60 weight percent V$_2$O$_5$, 5 to 40 weight percent MoO$_3$, 30 to 60 weight percent TiO$_2$, said carrier being alumina-silica or α-alumina having a surface area of less than about 1 square meter per gram, calcined at about 100° to 500° C over a 2- to 6-hour period maintaining said reaction zone and contents at a temperature between about 380° to about 450° C, maintaining said stream feed to said reaction zone and said oxygen at a gas hourly space velocity per hour (GHSV/hr$^{-1}$) at from between about 1,500 and about 15,000, said C$_5$ stream being from 0.5 to 1.5 volume percent of said total feed, withdrawing said products, cooling said product stream to condense the organic fraction therefrom, and recovering the maleic anhydride from said condensed fraction.

2. A process for preparing maleic anhydride which comprises treating a crude C$_5$ stream at a temperature of from 80° to 100° C for from about 8 to 32 hours, separating the resulting stream by distillation into an overhead of isoprene and piperylene and their closely related C$_5$ components, and a bottoms stream comprised predominantly of dicyclopentadiene and its codimers, introducing said bottoms stream and oxygen or oxygen-containing gas into a reaction zone containing a catalyst which comprises a mixture of vanadium oxide, molybdenum oxide, and titanium oxide supported on an inert carrier in an amount to supply from 3–20 weight percent of the mixture having a ratio of V$_2$O$_5$/MoO$_3$/TiO$_2$ of 25 to 60 weight percent V$_2$O$_5$, 5 to 40 weight percent MoO$_3$, 30 to 60 weight percent TiO$_2$, said carrier being alumina-silica or α-alumina having a surface area of less than about 1 square meter per gram, calcined at about 100° to 500° C over a 2- to 6-hour period maintaining said reaction zone and contents at a temperature between about 380° to about 450° C, maintaining said stream feed to said reaction zone and said oxygen at a gas hourly space velocity per hour (GHSV/hr$^{-1}$) at from between about 1,500 and about 15,000, said C$_5$ stream being from 0.5 to 1.5 volume percent of said total feed, withdrawing said products, cooling said product stream to condense the organic fraction therefrom, and recovering the maleic anhydride from said condensed fraction.

3. A process for preparing maleic anhydride which comprises treating a crude C$_5$ stream at a temperature of from 80° to 100° C for from about 8 to 32 hours, separating the resulting stream by distillation into an overhead containing all components boiling below dicyclopentadiene and its codimers separating by extractive distillation the piperylene and isoprene diolefins from said overhead, and fractionating the diolefins into an isoprene and a piperylene stream, feeding the piperylene stream together with the dicyclopentadiene/codimer fraction and oxygen or an oxygen-containing gas, into a reaction zone containing a catalyst which comprises a mixture of vanadium oxide, molybdenum oxide, and titanium oxide supported on an inert carrier in an amount to supply from 3–20 weight percent of the mixture having a ratio of V$_2$O$_5$/MoO$_3$/TiO$_2$ of 25 to 60 weight percent V$_2$O$_5$, 5 to 40 weight percent MoO$_3$, 30 to 60 weight percent TiO$_2$, said carrier being alumina-silica or α-alumina having a surface area of less than about 1 square meter per gram, calcined at about 100° to 500° C over a 2- to 6-hour period maintaining said reaction zone and contents at a temperature between about 380° to about 450° C, maintaining said stream feed to said reaction zone and said oxygen at a gas hourly space velocity per hour (GHSV/hr$^{-1}$) at from between about 1,500 and about 15,000, said C$_5$ stream being from 0.5 to 1.5 volume percent of said total feed, withdrawing said products, cooling said product stream to condense the organic fraction therefrom, and recovering the maleic anhydride from said condensed fraction.

* * * * *